United States Patent
Ow et al.

(10) Patent No.: US 11,473,425 B2
(45) Date of Patent: Oct. 18, 2022

(54) SURFACE LOGGING WELLS USING DEPTH-TAGGING OF CUTTINGS

(71) Applicant: Saudi Arabian Oil Company, Dhahran (SA)

(72) Inventors: Hooisweng Ow, Woburn, MA (US); Jason R. Cox, Ashland, MA (US); Martin E. Poitzsch, Northumberland, NH (US); Daniel T. Georgi, Houston, TX (US); Alberto F. Marsala, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 6 days.

(21) Appl. No.: 17/021,171

(22) Filed: Sep. 15, 2020

(65) Prior Publication Data

US 2020/0408089 A1 Dec. 31, 2020

Related U.S. Application Data

(63) Continuation of application No. 16/160,313, filed on Oct. 15, 2018, now Pat. No. 10,808,529.

(51) Int. Cl.
*E21B 47/04* (2012.01)
*E21B 49/00* (2006.01)
*G01N 30/72* (2006.01)
*G01N 33/28* (2006.01)

(52) U.S. Cl.
CPC ............ *E21B 49/005* (2013.01); *E21B 47/04* (2013.01); *G01N 30/7206* (2013.01); *G01N 33/2823* (2013.01)

(58) Field of Classification Search
CPC .............................. E21B 49/005; E21B 47/04
See application file for complete search history.

(56) References Cited

U.S. PATENT DOCUMENTS

| | | | |
|---|---|---|---|
| 8,627,902 | B2 | 1/2014 | Hammer |
| 9,366,099 | B2 | 6/2016 | Ly |
| 2004/0108110 | A1 | 6/2004 | Zupanick et al. |
| 2005/0252286 | A1 | 11/2005 | Ibrahim et al. |
| 2009/0087911 | A1 | 4/2009 | Rogerio |

(Continued)

FOREIGN PATENT DOCUMENTS

| | | |
|---|---|---|
| GB | 2489714 | 10/2012 |
| WO | 2014207075 | 12/2014 |
| WO | 2018085504 | 5/2018 |

OTHER PUBLICATIONS

GCC Examination Report issued in Gulf Cooperation Council Application No. GC 2019-3 8470, dated Jun. 27, 2021, 4 pages.

(Continued)

*Primary Examiner* — Taras P Bemko
(74) *Attorney, Agent, or Firm* — Fish & Richardson P.C.

(57) ABSTRACT

Systems and methods of surface logging a well use a plurality of polymeric taggants distinguishable from each other. The systems and methods can include adding each of the plurality of polymeric taggants in a repeating sequence to a circulating drilling fluid while drilling the well and taking a sample drill cuttings carried by the circulating drilling fluid. The systems and methods can also include measuring concentrations of individual polymeric taggants attached to the drill cuttings in the sample and identifying a depth associated with the sample based on the measured concentrations of individual polymeric taggants and on the sequence.

25 Claims, 10 Drawing Sheets

(56) References Cited

U.S. PATENT DOCUMENTS

2012/0062886 A1   3/2012   Piotti et al.
2012/0325465 A1  12/2012   Hammer et al.
2015/0132543 A1   5/2015   Nouzille et al.
2017/0059668 A1   3/2017   Chang et al.
2019/0368336 A1  12/2019   Hammond et al.

OTHER PUBLICATIONS

GCC Examination Report issued in Gulf Cooperation Council Application No. GC 2019-3 8470, dated Feb. 23, 2021, 5 pages.

Deschamps et al., "Drilling to the Extreme: the Micro-Coring Bit Concept," IADC/SPE 115187, presented at the IADC/SPE Asai Pacific Drilling Technology Conference and Exhibition. Aug. 25-27, 2008, 12 pages.

Desmette et al., "Drilling Hard and Abrasive Rock Efficiently, or Generating Quality Cuttings? You No Longer Have to Choose . . . ," SPE 116554, Society of Petroleum Engineers, 2008 SPE Annual Technical Conference and Exhibition, Sep. 21-24, 2008, 19 pages.

Georgi, et al., "Advances in Cuttings Collection and Analysis," SPWLA 34th Annual Logging Symposium, Jun. 13-16, 1993, 20 pages.

PCT International Search Report and Written Opinion in International Appln. No. PCT/US2019/056059, dated Feb. 21, 2020, 15 pages.

SURFACE LOGGING WELLS USING DEPTH-TAGGING OF CUTTINGS

CROSS-REFERENCE TO RELATED APPLICATIONS

This application is a continuation of and claims the benefit of priority to U.S. patent application Ser. No. 16/160,313, filed on Oct. 15, 2018, now U.S. Pat. No. 10,808,529, the contents of which are hereby incorporated by reference.

BACKGROUND

Surface logging (as known as mud logging) is the creation of a detailed record (well log) of a borehole by examining the cuttings of rock brought to the surface by the circulating drilling fluid (most commonly drilling mud). Surface logging provides well owners and producers with information about the lithology and fluid content of the borehole while drilling. Under some circumstances, foam or compressed air is employed as a circulating drilling fluid, rather than mud.

SUMMARY

This disclosure describes methods and systems for surface logging using depth-tagging of cuttings. These systems and methods can improve the quality of drilling cuttings analysis for cost-effective and safe formation evaluation and wellbore positioning during the drilling process.

In one aspect, methods of surface logging a well use a plurality of polymeric taggants distinguishable from each other. Each of the plurality of polymeric taggants is added to a circulating drilling fluid in a sequence while drilling the well. A sample of drill cuttings carried by the circulating drilling fluid is taken. Concentrations of individual polymeric taggants attached to the drill cuttings in the sample are measured. A depth associated with the sample based, at least in part, on the measured concentrations of individual polymeric taggants and on the sequence, is identified.

In one aspect, methods of surface logging a well use a plurality of polymeric taggants distinguishable from each other. Each of the plurality of polymeric taggants is added to a circulating drilling fluid while drilling the well in a repeating sequence. A sample of drill cuttings carried by the circulating drilling fluid is taken. The polymeric taggants have ceiling temperatures between 400 and 800 degrees centigrade (° C.). Ceiling temperature, Tc, indicates the temperature greater than which depolymerization (or unzipping of the polymer chain) of a specific polymer will occur and the polymer will revert to its monomer.

Embodiments of these methods can include one or more of the following features.

In some embodiments, the sequence is a repeating sequence including at least 5 polymeric taggants distinguishable from each other.

In some embodiments, portions of the polymeric taggants attach to the drill cuttings during generation of the drill cuttings. In some cases, adding each of the plurality of polymeric taggants to the circulating drilling fluid comprises adding nanoparticles of the polymeric taggants to the circulating drilling fluid. In some cases, the nanoparticles of the polymeric taggants penetrate into the drill cuttings.

In some embodiments, measuring concentrations of individual polymeric taggants attached to the drill cuttings in the sample comprises using pyrolysis-gas chromatography-mass spectrometry. In some cases, methods also include using pyrolysis-gas chromatography-mass spectrometry to analyze properties of the drill cuttings. In some cases, methods also include selecting polymeric taggants that have ceiling temperatures that do not interfere with pyrograms from source rock decomposition. In some cases, the polymeric taggants have ceiling temperatures between 400 and 800° C. In some cases, the polymeric taggants comprise styrenic polymers with ceiling temperature between 600 and 800° C. In some cases, the polymeric taggants comprise methacrylic polymers with ceiling temperature between 400 and 600° C. In some cases, pyrolysis-gas chromatography-mass spectrometry is used to simultaneously measure concentrations of individual polymeric taggants attached to the drill cuttings and analyze properties of the drill cuttings.

In some embodiments, methods also include performing nuclear-based porosity or mineralogy analyses on the drill cuttings.

In some embodiments, the polymeric taggants have an affinity for the drill cuttings. Affinity indicates that the polymeric taggants have surface functional groups that would lead to preferential attachment to the rocks/cuttings surfaces, for example, by columbic attraction, hydrophilic interactions, or hydrophobic interactions. In some cases, the polymeric taggants have a positively charged coating with an affinity for drill cuttings from siliciclastic reservoirs. In some cases, the polymeric taggants have a coating with an affinity for drill cuttings from carbonate reservoirs.

In some cases, the polymeric taggants have hydrophobic surfaces. For example, the polymer taggants can be in the form of nanoparticles or solubilized polymers. For polymer taggants in the form of nanoparticles, the native surface of the nanoparticles can be hydrophobic if the constituent monomers are hydrophobic (for example, styrene, methylstyrene, butyl methacrylate, etc.) or the nanoparticles can be coated with a hydrophobic polymer. For polymer taggants in the form of solubilized polymers such as, for example, polystyrene or low density polyethylene that are soluble in diesel, the polymer is hydrophobic.

In some embodiments, taking the sample of the circulating drilling fluid comprises taking the sample before the drilling fluid returns to a mud pit or other reservoir.

In some embodiments, adding each of the plurality of polymeric taggants to a circulating drilling fluid comprises injecting fluid bearing the polymeric taggants at a concentration of between 500 and 1500 parts per million (ppm) by mass at a rate of between 1 and 10 liters per minute into the mud-flow. In some cases, injecting fluid bearing the polymeric taggants comprises injecting fluid bearing a first polymeric taggant for between 30 and 180 seconds (s) before switching to a next polymeric taggant. In some cases, switching to the polymeric taggant next in the sequence comprises waiting between 60 and 240 seconds after stopping injection of the first polymeric taggant before starting injection of the next polymeric taggant. In some cases, methods also include bagging cuttings at intervals of between 5 and 8 meters. In some cases, the circulating drilling fluid comprises drilling mud. In some cases, the circulating drilling fluid comprises foam.

These systems and methods can tag drill cuttings as they are cut at the bit face with a sequence of taggants that adhere to drill cuttings, penetrate into drill cuttings, or both. The downward trip time for the drilling fluid and associated tags through the drill pipe or coil can be calculated with a high degree of accuracy (for example, +/−3 feet, +/−2 feet, or +/−1 foot) enabling individual taggants of the sequence of taggants to be correlated with specific depths. In addition, the adherence to or penetration into the drill cuttings by these taggants enables the identification of the depth of origin of drill cuttings being analyzed even if the drill cuttings are shifted or scrambled in transport or storage.

By taking advantage of the high sensitivity analysis provided by pyrolysis-GCMS (gas chromatography-mass spectrometry) instrumentation, the described taggants are detectable and identifiable at low concentrations even in the presence of the most interfering contaminants characteristic of the drilling process (for example, water, high salt concentrations, diesel and other oily drilling fluid base constituents) without any sophisticated cleaning or separation process or work-up. Potentially, the analysis can be done in near-real-time. For example, an onsite surface logging unit directly connected to the drilling fluid circulation can provide depth correlation for drill cuttings minutes after delivery of samples of the drill cuttings.

The details of one or more embodiments of these systems and methods are set forth in the accompanying drawings and the description. Other features, objects, and advantages will be apparent from the description and drawings, and from the claims.

DESCRIPTION OF DRAWINGS

Like reference symbols in the various drawings indicate like elements.

DETAILED DESCRIPTION

This disclosure describes methods and systems of surface logging used for formation analysis while drilling wells. These systems and methods use a sequence of taggants that attach to (for example, adhere to, penetrate into, or both) drill cuttings as the drill cuttings are produced by operation of a downhole drill bit. The downward trip time for the drilling fluid and associated taggants through the drill pipe or coil can be calculated with a high degree of accuracy enabling individual taggants of the sequence of taggants to be correlated with specific depths (for example, +/−3 feet, +/−2 feet, or +/−1 foot). The attachment of the taggants to the drill cuttings enables the identification of the depth of origin of drill cuttings being analyzed, even if the drill cuttings are shifted or scrambled in transport or storage.

Figure 1:
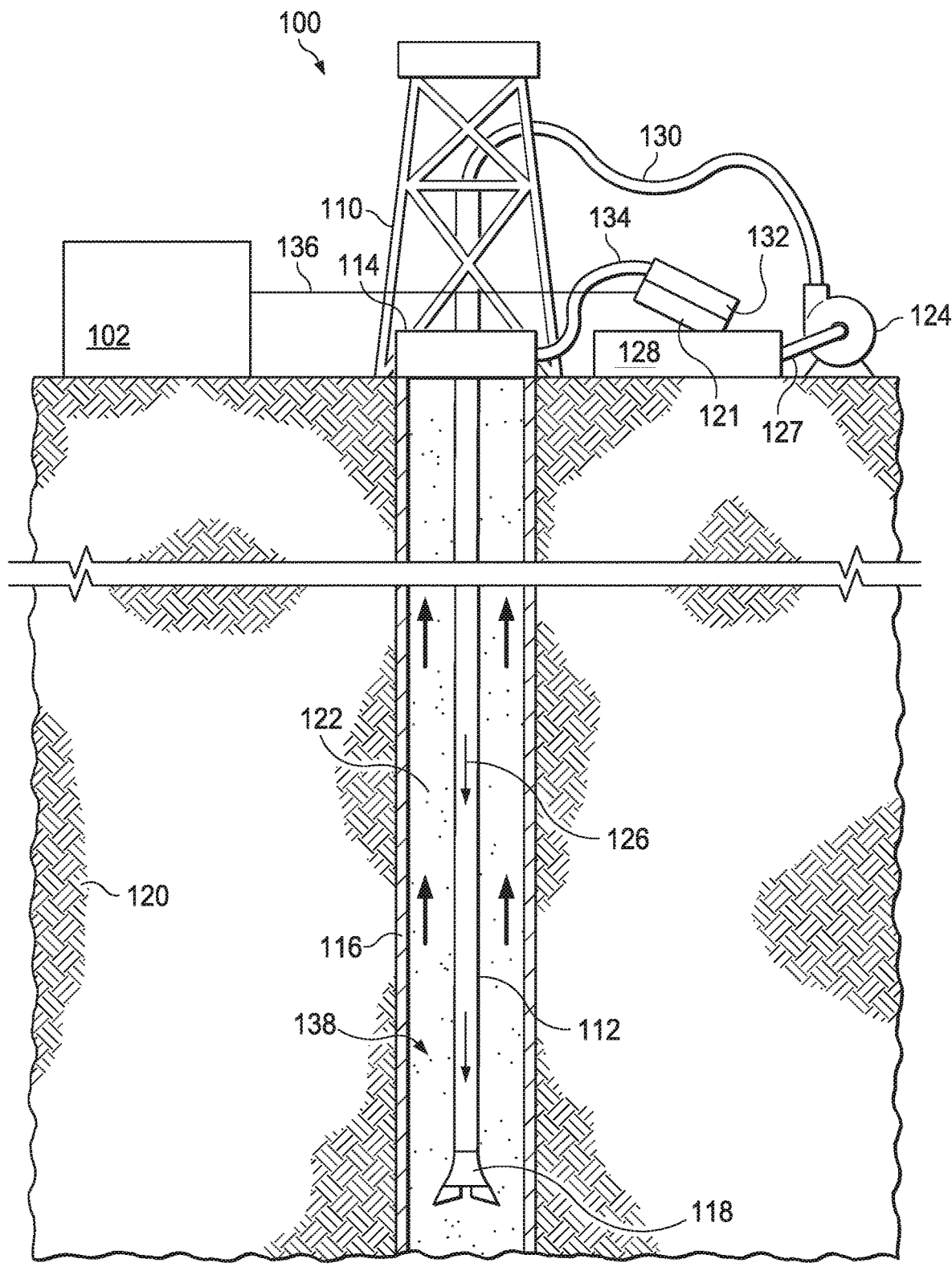
FIG. 1 is a surface logging operation with a surface logging unit.

FIG. 1 shows a drilling system 100 and an associated surface logging unit 102. The drilling system 100 includes a derrick 110 that supports the weight of and permits selective positioning of a drill string 112 through a blowout preventer 114 at the wellhead of a wellbore 116. The drill string 112 has a downhole end coupled to a drill bit 118 operable to drill the wellbore 116 in a formation 120. To facilitate drilling and removal of drill cuttings 122, a circulation pump 124 circulates drilling fluid 126 though the wellbore 116. An inlet of a circulation pump 124 is coupled to a reservoir for the drilling fluid through a first pipe 127. In the illustrated system, the reservoir is a mud pit 128. In some systems, reservoir can be, for example, a tank or tanks. An pump discharge of the circulation pump 124 is coupled to a top end of the drill string 112 through a second pipe 130. The blowout preventer 114 is coupled to a shaker table 132 through a third pipe 134. The mud pit 128 is coupled to the shaker table 132 and receives the drilling fluid 126 from the shaker table 132.

In the optional case of real-time well-site logging of cuttings, a suction line 136 or other continuous transfer line couples the surface logging unit 102 with the shaker table 132. The surface logging unit 102 includes analytical equipment operable to identify taggants 138 associated with the drill cuttings 122 and perform petro-physical analysis on the drill cuttings 122. For example, the surface logging unit 102 includes a pyrolysis-GCMS, densitometers, an X-ray diffractometer, a fluorescence spectrometer, and other mineralogical analysis instruments, as well as sample cleaning equipment.

The surface logging unit 102 is onsite and directly coupled to the drilling fluid circulation system. This configuration facilitates near-real-time depth information. For example, an onsite surface logging unit directly coupled to the drilling fluid circulation can provide depth correlation for drill cuttings within minutes after delivery of samples of the drill cuttings.

During drilling, the drilling fluid 126 is pumped from the mud pit 128 and flows through the first pipe 127 into the pump suction of the circulation pump 124. The circulation pump 124 then pumps the drilling fluid 126 from the pump discharge to the top end of the drill string 112 through the second pipe 130. The sequence of taggants 138 is introduced into the drilling fluid 126 between the circulation pump 124 and the blowout preventer 114 or between the mud pit 128 and the circulation pump 124.

Figure 2:
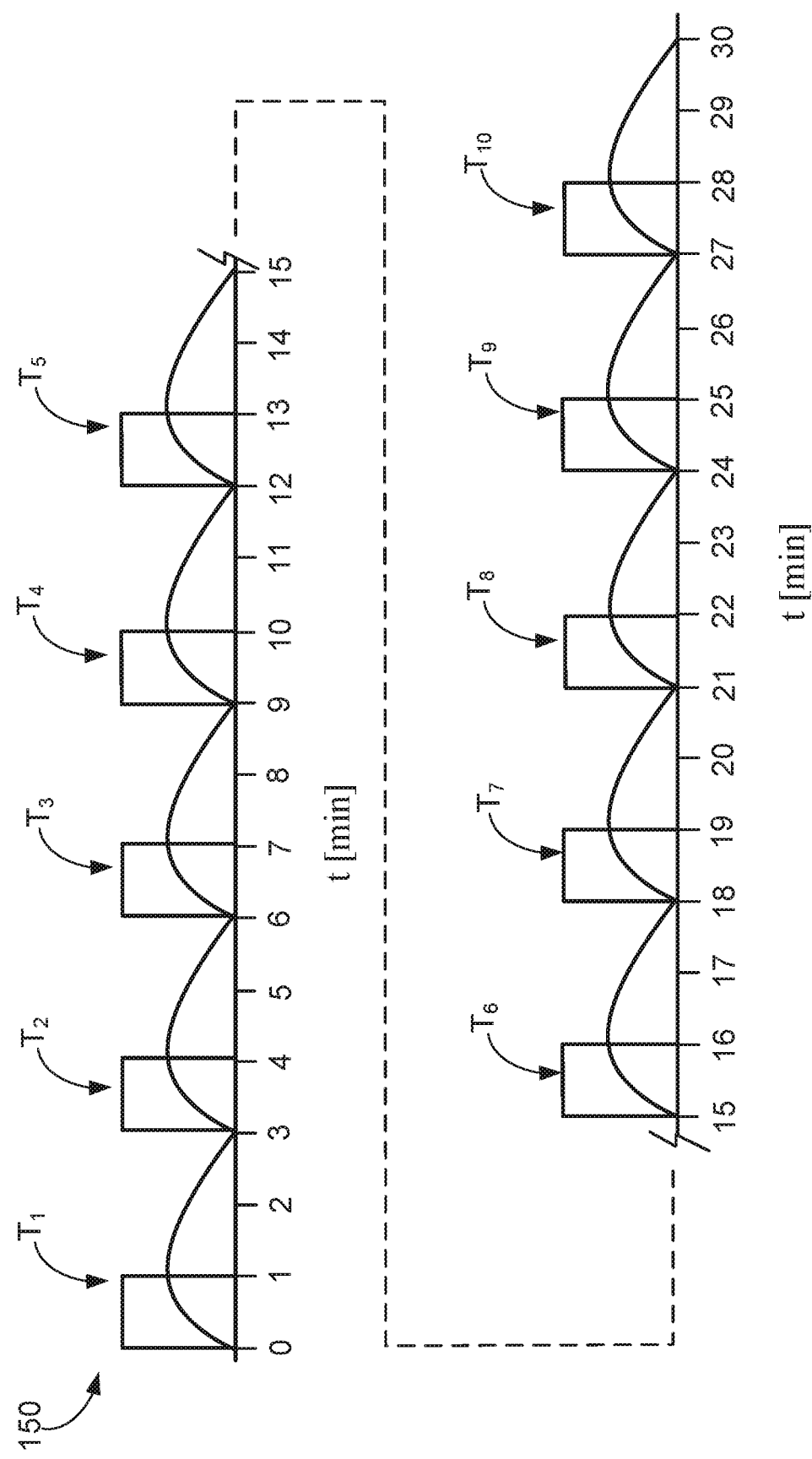
FIG. 2 is a schematic illustrating a taggant injection sequence.

FIG. 2 illustrates an exemplary sequence 150 of 10 distinct taggants being introduced into drilling fluid. In the sequence 150, the taggants ($T_1 \ldots T_{10}$) are introduced in pulses with each taggant being added for one minute followed by a two-minute pause before addition of the next taggant begins. The significance of the multiple unique taggants and timing of injection is discussed in more detail later in this disclosure.

Referring again to FIG. 1, the drilling fluid 126 carrying the taggants 138 flows downhole in the drill string 112 through the wellhead and the blowout preventer 114 and enters the wellbore 116 through the drill bit 118. As the drilling fluid 126 exits the drill bit 118, the taggants 138 attach to the drill cuttings 122 being produced by the drill bit 118. The drilling fluid 126 flows through the wellbore annulus toward the wellhead while carrying the drill cuttings 122 and the attached taggants 138. The drilling fluid 126 flows through the blowout preventer 114 to the shaker table 132 through the third pipe 134. The shaker table 132 removes the drill cuttings 122 and the attached taggants 138 from the drilling fluid 126 before the drilling fluid 126 flows to the mud pit 128. At least a portion of the drill cuttings 122 and the attached taggants 138 are transferred to the surface logging unit 102 for analysis to identify the depth of origin and petro-physical properties of the drill cuttings 122.

While the illustrated implementation shows a vertical wellbore, the principles of this disclosure can also be applied to a deviated or horizontal wellbore or to a drilling system that uses coiled tubing drilling.

Figure 3:
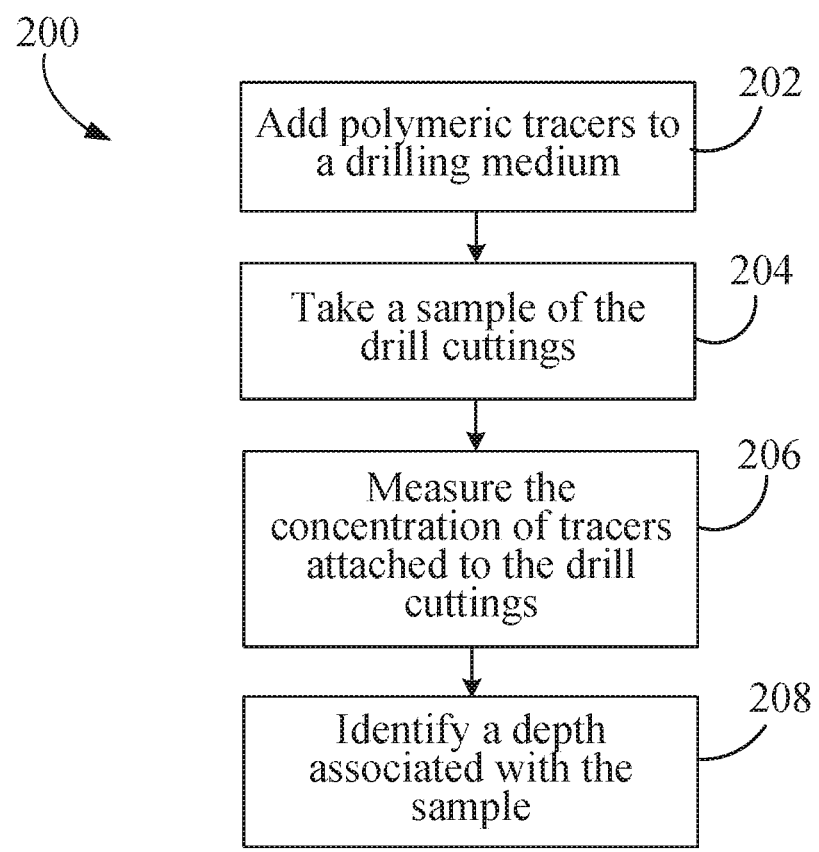
FIG. 3 is a flowchart illustrating a surface logging method.

FIG. 3 shows a flowchart of an example method 200 that can be used to identify the depth of origin and petro-physical properties of drill cuttings. The method 200 is described with reference to the drilling system 100 and surface logging unit 102 and their components shown in FIG. 1 and the sequence of taggants shown in FIG. 2.

The surface logging unit 102 performs surface logging as a drilling system 100 is being used to form a wellbore 116 using a plurality of taggants 138 distinguishable from each other. Theoretically, optically barcoded taggants could be used. However, optical signals might be harder to read out reliably due to the opaque nature of drilling mud. Each of the plurality of taggants 138 is added to circulating drilling fluid 126 in a sequence while drilling proceeds (step 202). The taggants 138 are added to the drilling fluid 126 between the circulation pump 124 and the blowout preventer 114. The sequence can be a repeating sequence in which the sequence restarts after the last taggant in the sequence is added to the drilling fluid.

The polymeric taggants can be added to the circulating drilling fluid by injecting fluid bearing the polymeric taggants at a concentration of between 500 and 1500 ppm at a rate of between 1 and 10 liters per minute into the flow of the drilling fluid. The addition can include injecting fluid bearing a first polymeric taggant for between 30 and 180 seconds before switching to the next polymeric taggant in the sequence. Typically, the switching includes waiting between 60 and 240 seconds after stopping injection of the first polymeric taggant before starting injection of the next polymeric taggant.

Portions of the taggants 138 attach to the drill cuttings 122 during generation of drill cuttings 122. In some cases, the plurality of taggants 138 are added to the circulating drilling fluid 126 in the form of nanoparticles of the taggants 138. In these cases, the nanoparticles can be between 1 nanometer (nm) to 100 nm in size (for example, between 10 nm and 50 nm in size). The nanoparticles of the taggants 138 can adhere to drill cuttings, penetrate into drill cuttings, or both. It is desirable that that the taggants have an affinity for the drill cuttings. For example, the taggants can have: a positively charged coating with an affinity for drill cuttings from siliciclastic or unconventional shale reservoirs; a coating with an affinity for drill cuttings from carbonate reservoirs; a hydrophobic surface; or some combination of these characteristics. Note that the drilling mud type (oil-based mud, water-based mud) will also influence the taggants' surface chemistry design.

When the circulating drilling fluid 126 returns to the surface, samples of drill cuttings 122 are taken (step 204). The samples are typically taken after the drilling fluid returns to the surface and before the drilling fluid returns to a mud pit or other reservoir. For example, taking the samples can include bagging cuttings at intervals of between 5 and 8 meters of the advance of the wellbore. In another example, taking the samples can include taking samples of the circulating drilling fluid 126 that includes the drill cuttings.

The samples are analyzed to measure concentrations of individual polymeric taggants attached to the drill cuttings 122 in the sample (step 206). A given taggant is positively identified when it is significantly (typically over 3×) greater than any background "noise" signals from natural geological species or cross-pollution from taggants in reused drilling mud. Pyrolysis-GCMS can be used to measure concentrations of individual polymeric taggants attached to the drill cuttings in the sample. Pyrolysis-GCMS can also be used to analyze properties of the drill cuttings. This combined approach can enable simultaneous identification of origin depth and composition characteristics of drill cuttings. This combined approach is facilitated by selecting polymeric taggants that have ceiling temperatures that do not interfere with pyrograms from source rock decomposition. The selected polymeric taggants can have ceiling temperatures between 400 and 800° C. For example, the polymeric taggants can be styrenic polymers with ceiling temperature between 600 and 800° C. or methacrylic polymers with ceiling temperature between 400 and 600° C.

Nuclear-based porosity or mineralogy analyses can also be performed on the drill cuttings. In contrast to elemental taggants, the polymeric taggants typically do not interfere with analyses such as, for example, x-ray refraction or other nuclear-based porosity or mineralogy analyses conventionally performed on reservoir rock cores and drill cuttings.

Based at least in part on the measured concentrations of individual polymeric taggants and on the sequence, depths associated with the samples are identified (step 208).

The method 200 can be used when the drilling system 100 uses drilling mud as a drilling fluid. The method 200 can also be used when the drilling system 100 uses foam as a drilling fluid. Using polymeric taggants can enable surface logging of drilling using light underbalanced foams since some polymeric taggants are similar in density to water. For example, polystyrene has a density of approximately 1.04 grams per cubic centimeter (g/cc) and polymethacrylate has a density of approximately 1.18 g/cc. In contrast, denser taggants such as silica or metal oxides with density equal to or more than 2× that of water are not usable with light underbalanced foams.

As discussed previously, this disclosure shows taggants that attach into the drill cuttings as they are generated. The approach keeps the taggants with the labeled cuttings during collection and transport to the actual point of analysis. That reduces and can eliminate possible depth interpretation errors associated with settling or separation of tags from cuttings that can occur with larger ceramic or shell tags. In addition, the intrinsic depth uncertainty, du, is much smaller when the tags are applied at the point of cuttings generation (that is, at the drill bit) than when the depths are merely estimated from the arrival of the cuttings at the shaker screen. The key is the larger difference in lag-time between downward travel of a pulse of tags and the upward return travel of the cuttings in the annular mud returns. In the disclosed method, tags are injected into the mud at time $t_o$, and the original depth of the cuttings in which they are embedded will be interpreted to be the rig's recorded bit depth at time $t_o+t_{down}$, where $t_{down}$ is the time of downward travel of the mud in the pipe. The difference in depth between these two times is approximately $v*t_{down}$, where v is the drilling rate of penetration. The potential error in depth will be a fraction of that difference. A conservative estimate of the potential error in depth is $(v*t_{down})/2$. In the conventional method, the original depth of the cutting arriving at the shaker screen is estimated using a calculated upward travel time, $t_{return}$. The depth difference $(v*t_{return})$ between the bit depth at cuttings generation and the bit depth at cuttings retrieval is much larger yielding an order of magnitude greater depth uncertainty, du. In addition, there can be differential settling effects and geometric non-idealities in the open hole annular volume (for example, over-gauge hole conditions, washouts or caves), causing additional unknown errors. Table 1 presents characteristics and estimated depth uncertainty for an exemplary drilling operation.

TABLE 1

Depth Correlation in Mud-Logging

| Inputs | | |
|---|---|---|
| Drillpipe/tubing ID | 1.5 inches | (0.038 meters) |
| Mud flow-rate | 400.0 gallons/minute (gpm) | (0.025 meters^3/second) |
| Drillpipe/tubing OD | 3.0 inches | (0.076 meters) |
| Hole diameter | 6.0 inches | (0.152 meters) |
| Drilling rate (v) | 100.0 feet/hour | (1.667 feet/minute) |
| Vertical section depth | 6000.0 feet | (1828.8 meters) |
| Horizontal step-out | 5000.0 feet | (1524.0 meters) |
| Total depth | 11000.0 feet | (3352.8 meters) |
| Calculated | | |
| Internal flow velocity | 72.6 feet/second | (22.1 meters/second) |
| Annular flow velocity | 6.1 feet/second | (1.8 meters/second) |
| Outputs | | |
| Time to bit ($t_{down}$) | 2.5 minutes | |
| Time to surface ($t_{return}$) | 30.3 minutes | |
| Depth uncertainty down | 2.1 feet | (0.6 meters) |
| Depth uncertainty return | 25.2 feet | (7.7 meters) |

This strategy takes advantage of the unique circumstances that exist during surface logging. The drilling fluid is constantly recycled during operations, and taggants gradually accumulate in the drilling fluid. Taggants added to the drilling fluid in quantities to be identifiable in the collected cuttings can eventually accumulate to background levels that make it unclear when the taggant was added and at what depth a sample is correlated. By using taggants that are detectable at low limits of detection and that have an affinity for the drill cuttings, the systems and methods described in this disclosure reduce the total volumes of taggants that need to be added to drilling fluid for surface logging. Using GCMS as a detector, the low end of the detection limit is anticipated to be between hundreds of parts-per-trillion (ppt) and tens of parts-per-billion (ppb). State-of-the-art triple quadrupole mass spectrometer may be able to achieve ppt detection levels. A single quadrupole mass spectrometer or a flame ionization detector (FID) on the gas chromatograph may be able to achieve one ppb detection limits.

Using unique particle compositions for each new drill string added during a surface logging operation would be the most straightforward approach, but is not feasible due to cost constraints and limitations on the number of commercially available monomers. The sequential strategy solves this challenge by adding the taggants in concentrated form at the drill string and collecting the taggants at the shaker before the drilling fluid is diluted into the mud pit. With knowledge of the mud pit volume, and the lower limit of detection of the taggants, previously used taggants can be added in sequence until the concentration of individual taggants in the mud pit or other drilling fluid reservoir begins to approach the lower limit of detection.

The example sequence 150 discussed with reference to FIG. 2 has 10 taggants that are introduced in one-minute pulses followed by a two-minute pause before addition of the next taggant begins. Other sequences may have other numbers of taggants or different delivery timings. The number of the taggants in the sequence, the timing of their delivery, and the delivery concentrations are determined based on factors including, for example, the drilling rate, the feasible taggant injection rate into the mud pipe, the fluid circulation rate, the drill string/tubing inner diameter (ID) and the taggant detection sensitivity limits.

A volume of taggants is added to the drilling fluid to provide a concentration of an individual taggant at the drill bit greater than the limit of detection for the taggant. The delivery concentration of taggants and length of delivery pulse is chosen to provide this volume of taggants. This approach supports identification of the origin depth of cuttings the taggants are attached to while limiting the previously described problems associated with accumulation of taggants in the drilling fluid. The gap between pulses is typically chosen such that the concentration of a taggant at the bit approaches zero before delivery of the next taggant starts at the surface. The appropriate volume of taggant per pulse can be estimated by multiplying the volume of drilling fluid per pulse times the limit of detection for the taggant. Dividing the volume of taggant per pulse by the concentration of the taggant bearing injection fluid provides the necessary volume of the taggant bearing injection fluid.

For example, the drilling operation described with reference to Table 1 has a drilling rate 100 feet/hour (30.48 meters/hour) and a mud flow-rate of 400 gpm (0.025 cubic meters/second). At a total depth of 11,000 feet (3350 meters), the time to bit is approximately 2.5 minutes. For this situation, a 1-minute pulse of taggant with a 2-minute separation pause would likely be appropriate. At this mud flow-rate, the volume of drilling fluid associated with the 1-minute pulse would be approximately 400 gallons (1.5 cubic meters). Delivering 0.5 gallons (2 liters) of fluid bearing the taggant at a concentration of 1000 ppm in this pulse would provide a taggant concentration of a little over 1 ppm at the drill bit.

Injecting taggants at 1-3 gpm and switching taggants between pulses can be accomplished using a small manifold of tanks containing the individual taggant fluid suspensions that are switched in an automatic, regularly cycling way into an injection pump. If the pump is a low-pressure injection pump, the pump can inject the taggant at the input to high-pressure drilling fluid mud pumps. If the pump is a high-pressure injection pump, the pump can be coupled to an injection manifold in the high-pressure portion of the mud line. This approach enables the rapid switching between taggants that supports the systems and methods described in this disclosure. In contrast, systems and methods that introduce taggants into the drilling fluid reservoir have slower switching due to the volume of drilling fluid reservoir.

Pumping a given taggant for about a minute would mark one to three feet of formation cuttings at typical drilling rates of penetration. Cuttings could be bagged off the shakers every twenty feet or so. Such a bag, labeled by time and nominal bit-depth, would contain some six to ten different taggants in its cuttings. Choosing the bagging interval so that each taggant occurs only in one time-window in the bag (for example, the number of taggants in each bag is smaller than the total number of taggants used) reduces the likelihood of confusion between depth intervals The taggants can be polymers with known ceiling temperatures. For example, the taggants can be in the form of polymeric nanoparticles or solubilized polymers depending on how the polymers are produced (emulsion polymerization for the former and solution polymerization for the latter). Emulsion polymerization produced discreet nanoparticles whereas bulk or solution polymerized materials, unless cross-linked, are usually free polymer chains. The polymeric nanoparticles can be made via emulsion polymerization where the polymers are usually dispersed oil droplets suspended in an aqueous solution of surfactants. The polymeric nanoparticle are suspended in oil-based or water-based muds in a presence of compatibilizing surfactant(s). Solubilized polymers refer to polymers that have been polymerized in bulk or in solution without the presence of a surfactant. In the case of solution polymerization, both the monomer and the polymers are soluble in the solvent. The solubilized polymers include free polymer chains that are soluble in oil-based or water-based drilling muds.

Polymeric nanoparticle taggants for use with these systems and methods can be formed by the synthesis of the nanoparticles using emulsion polymerization technique. The semi-continuous monomer-starved addition methodology used relies on the restriction of monomer feed rate to obtain tightly controlled sizes of the resulting ultra-small nanoparticles (sub-50 nanometer) using minimal amounts of inexpensive surfactants with relatively high solid yield (over 7500 ppm). Solid yield refers to the yield of solid polymer in a synthesis determined with thermal gravimetric analysis. The polymerization technique is versatile and extendable to different types of monomers, including a variety of styrenic and methacrylic monomers. These techniques are described in more detail in PCT Pat. App. Ser. No. PCT/US2017/059668, incorporated by reference in its entirety.

Styrenic monomers include, but are not limited to, 4-Acetoxystyrene, 4-Benzhydryl styrene, 4-Benzyloxy-3-methoxystyrene, 4-tert-Butoxystyrene, 4-Bromostyrene, 4-Chlorostyrene, 2,6-Dichlorostyrene, 2,6-Difluorostyrene, 3,4-Dimethoxystyrene, 2,4-Dimethyl styrene, 4-Ethoxystyrene, 4-Flourostyrene, 4-Methylstyrene, α-Methylstyrene, Pentafluorophenyl 4-vinylbenzoate, 2,3,4,5,6-Pentafluorostyrene, 4-(Trifluoromethyl)styrene, 2,4,6-Trimethylstyrene, 4-Methoxystyrene, 4-Vinylbenzocyclobutene, 4-Chloromethyl styrene, 4-Vinylbiphenyl, 4-Vinylbenzoic acid, 1,1-Diphenylethylene, 3,5-Bis(trifluoromethyl)styrene, 4-Vinylphenyl acetate, and Trimethoxy(4-vinylphenyl)silane. Aminostyrenic monomers include, but are not limited to, (1S)-1-(3-vinylphenyl)-1,2-ethanediamine and 4-vinylphenol.

Methacrylic monomers include, but are not limited to, 1-naphthyl methacrylate, pentabromophenyl methacrylate, phenyl methacrylate, propyl methacrylate, stearyl methacrylate, 3-sulfopropyl methacrylate potassium salt, tetrahydrofurfuryl methacrylate, 3,3,5-trimethylcyclohexyl methacrylate, 1,1,1,3,3,3-hexafluoroisopropyl methacrylate, 2,2,3,4,4,4-hexafluorobutyl methacrylate, 2,2,3,3,4,4,4-heptafluorobutyl methacrylate, 2-[(1',1',1'-trifluoro-2'-(trifluoromethyl)-2'-hydroxy)propyl]-3-norbornyl methacrylate, 2,2,2-trifluoroethyl methacrylate, 3,3,4,4,5,5,6,6,7,7,8,8,8-tridecafluorooctyl methacrylate, 2,2,3,3-tetrafluoropropyl methacrylate, 2,2,3,3,3-Pentafluoropropyl methacrylate, 2,2,3,3,4,4,5,5-Octafluoropentyl methacrylate, and 1,1,1,3,3,3-Hexafluoroisopropyl methacrylate.

Polymeric taggants can also be formed from reacting amine-containing styrenic monomer, such as 4-Vinylaniline, with epoxide monomers. Epoxide monomers include, but are not limited to 1,2-Epoxybutane, 1,2-Epoxypentane, 1,2-Epoxyhexane, 1,2-Epoxyoctane, 1,2-Epoxydodecane, 1,2-Epoxytetradecane, 1,2-Epoxyhexadecane, 2-Hexadecyloxirane, Allyl glycidyl ether, Butyl glycidyl ether, tert-Butyl glycidyl ether, 3,4-Epoxy-1-butene, 1,2-Epoxy-5-hexene, 1,2-Epoxy-9-decene, 4-Chlorophenyl glycidyl ether, 1,2-Epoxy-3-phenoxypropane, (2,3-Epoxypropyl)benzene, 2-Ethylhexyl glycidyl ether, Furfuryl glycidyl ether, Glycidyl hexadecyl ether, Glycidyl isopropyl ether, Glycidyl 4-methoxyphenyl ether, Glycidyl 2-methylphenyl ether, Glycidyl 2,2,3,3,4,4,5,5-octafluoropentyl ether, 2,3-Epoxy-1-(1-ethoxyethoxy)propane, 1,2-Epoxydecane, 1,2-Epoxyoctadecane, 1,2-Epoxyeicosane, 2,2,3,3,4,4,5,5,5-Nonafluoropentyloxirane, 2,2,3,3,4,4,5,5,6,6,7,7,7-Tridecafluoroheptyloxirane, 1,2-Epoxy-1H,1H,2H,3H,3H-heptadecafluoroundecane, Glycidyl methyl ether, Ethyl glycidyl ether, Epichlorohydrin, Glycidyl propargyl ether, Glycidyl lauryl ether, tert-Butyldimethylsilyl (S)-glycidyl ether, 3-Glycidyloxypropyltrimethoxysilane, 3-Glycidyloxypropyl(dimethoxy)methylsilane, [8-(Glycidyloxy)-n-octyl]trimethoxysilane, Triethoxy(3-glycidyloxypropyl)silane, Diethoxy(3-glycidyloxypropyl)methylsilane, 1,1,1,3,5,5,5-Heptamethyl-3-(3-glycidyloxypropyl)trisiloxane, 3-[2-(Perfluorohexyl)ethoxy]-1,2-epoxypropane, Benzyl glycidyl ether, 4-tert-Butylphenyl glycidyl ether, 2,4-Dibromophenyl glycidyl ether, (S)-Glycidyl titryl ether, (S)—N-Glycidylphthalimide, and 4-Glycidyloxycarbazole These techniques can also provide taggants with selective surface functionality. For example, polymeric taggants can be surface functionalized with glycidylated polyethylenimine to impart colloidal stability in brines. The polymeric taggants can also be surface functionalized to reduce retention to reservoir rocks and keep the nanoparticles stable/suspended in the hot briny environment so that the nanoparticles can be transported deep into the reservoir with injected water. Similarly, the wettability of the nanoparticle tags can be tuned by surface functionalization to perform with optimal cuttings penetration in either oil-base or water-base mud systems. For example, a positively charged polyethylenimine coating will have affinity for drill cuttings from siliciclastic reservoirs. Surface functionalization tailoring affinity toward drill cuttings from carbonate reservoirs (for example, coatings with functional groups such as phosphonates and carboxylates) can be engineered as well. The surface of the nanoparticles may also be selectively hydrophobized for compatibilization with oil-based muds, and impregnation into cuttings with mixed-wettability.

These polymeric taggants can be identified using pyrolysis-GCMS. In these systems, the volatility of oil and water permits a pre-drying step where the contaminants are removed prior to decomposition of the tags into monomers. As previously discussed, detectability of these polymeric nanoparticles is depends on the GCMS instrument being used and is typically less than at 1 ppm. Using GCMS as a detector, the low end of the detection limit is anticipated to be between hundreds of parts-per-trillion (ppt) and tens of parts-per-billion (ppb). State-of-the-art triple quadrupole mass spectrometer may be able to achieve one ppt detection levels. A single quadrupole mass spectrometer or a flame ionization detector (FID) on the gas chromatograph may be able to achieve one ppb detection limits. The taggants are detectable and decodable at low concentrations even in the presence of the most obfuscating contaminants characteristic of the drilling process (water, high salt concentrations, diesel and other oily drilling fluid base constituents) without any sophisticated cleaning or separation process or work-up. Potentially, this analysis could even be done in near-real-time on or near the rig-site.

The proposed polymer-based nanoparticulate taggant material is low-cost and low-density, therefore, easy to convey even with light underbalanced drilling foams and easy to embed into the cuttings pores, even the tiny pores of tight formations and unconventional reservoirs. For purposes of this disclosure, unconventional reservoirs include, for example, shale oil or shale gas reservoir. The feasibility of this approach was demonstrated by pyrolyzing as-is drill cuttings from unconventional reservoir injected with various polystyrene-based taggants.

FIGS. 4A-4F show gas chromatograms of various styrenic polymer nanoparticles detected in the presence of drill cuttings. Pyrolysis was conducted using an AS 5250 pyrolysis autosampler from CDS Analytical. 10 uL of polymer solution sample was added to 10 mg of solid drill cuttings and allowed to dry in air. After this, the drill cutting samples were loaded into a thin closed-end tube filled with quartz wool. The drying temperature was set to 400° C. for 20 seconds followed by pyrolysis at 800° C. for 15 seconds. These gas chromatograms were produced with a flame ionization detector. The intensity is in micro-volts (µV) and the x-axis is retention time of the analyte in a given column under a given analysis condition. In these figures, the monomer symbol in each graphs represents the monomer repeating unit of the styrenic polymer nanoparticle analyzed. After thermally degrading/pyrolyzing the polymers at their ceiling temperatures, the product is primarily from polymer reversion to its monomer.

Figure 4A:
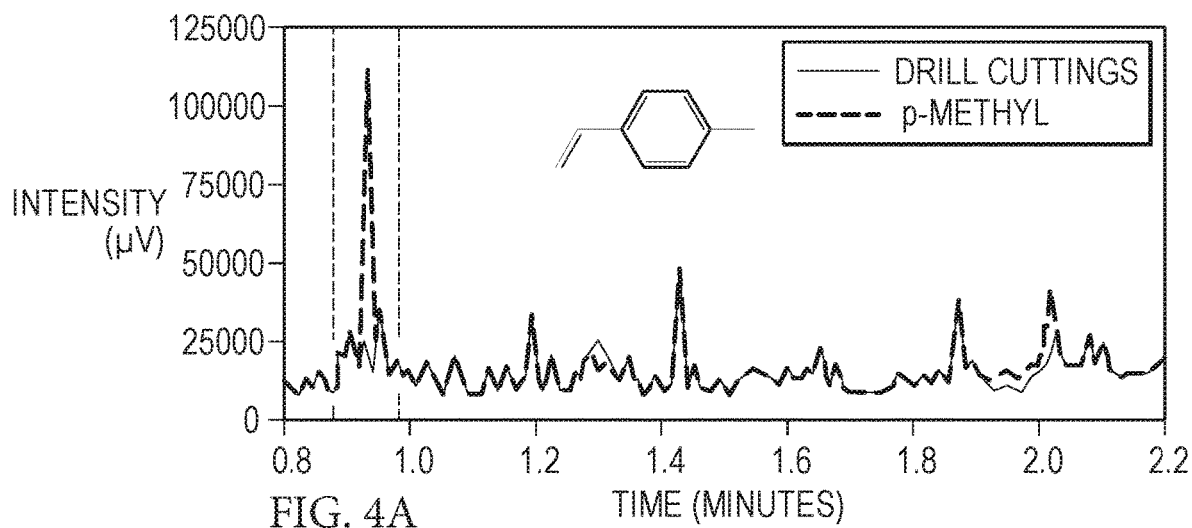
FIGS. 4A-4F show gas chromatograms of various styrenic polymer nanoparticles detected in the presence of drill cuttings.
Figure 4B:
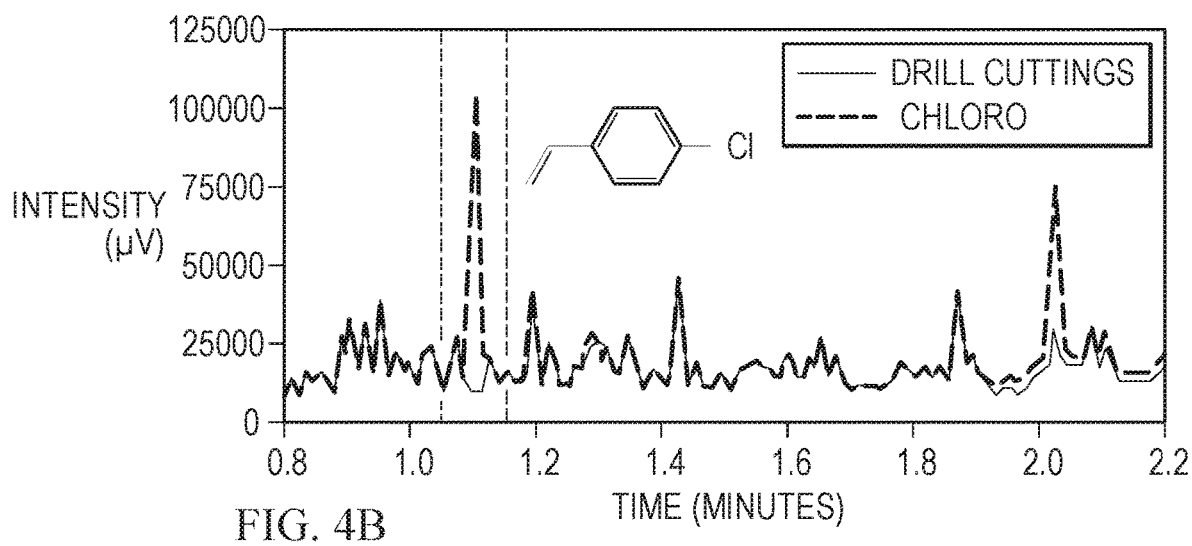
Figure 4C:
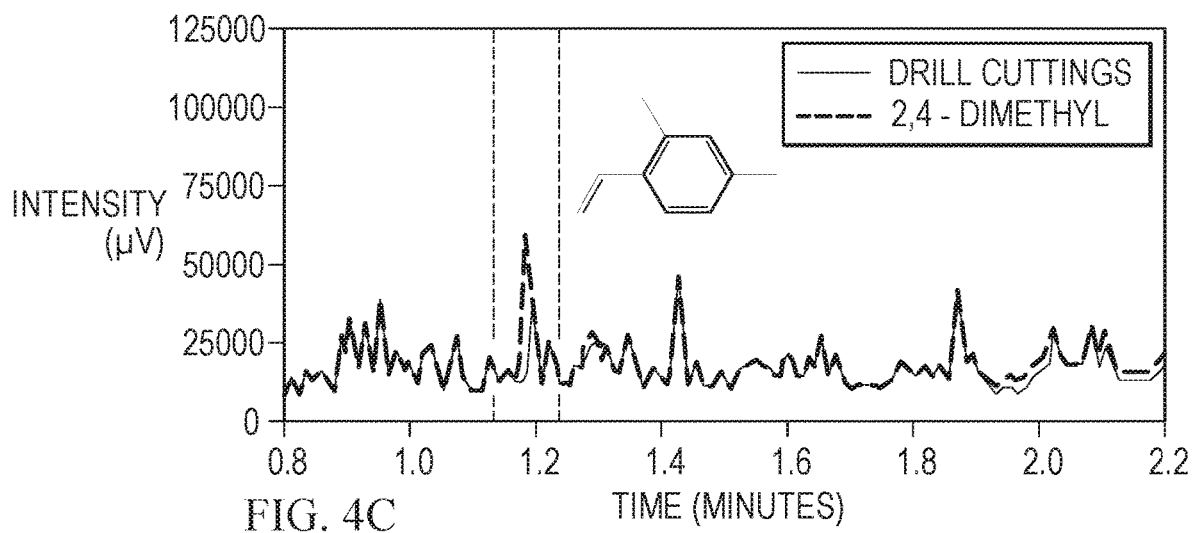
Figure 4D:
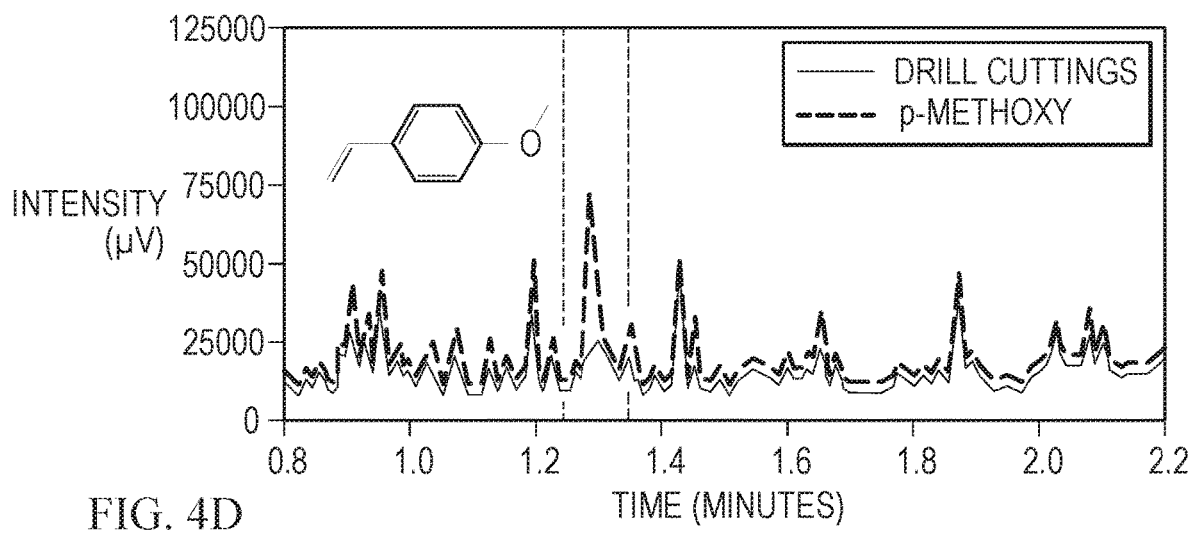
Figure 4E:
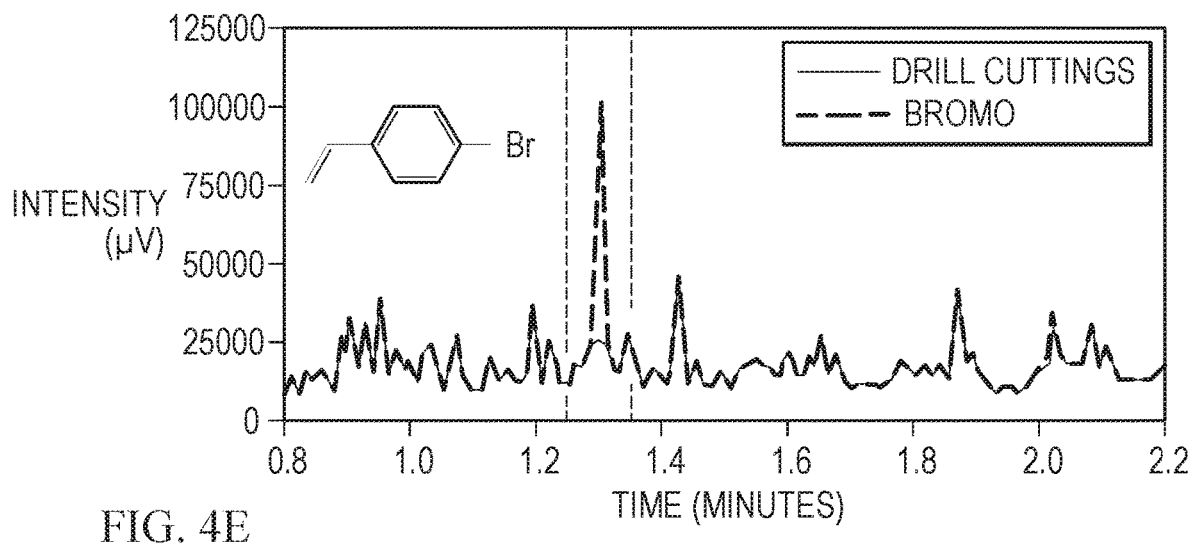
Figure 4F:
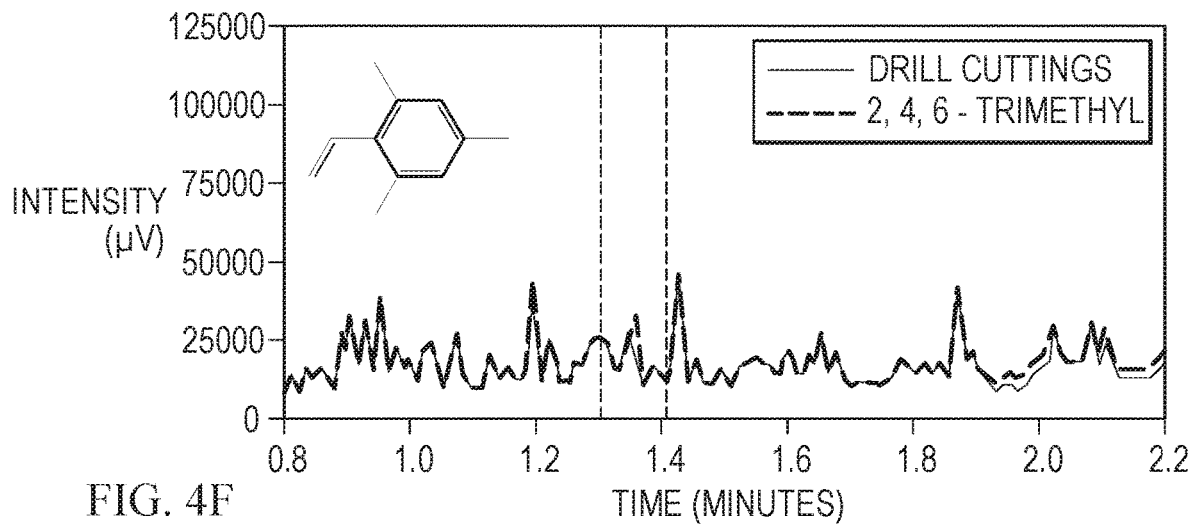

In this test, various styrenic polymer nanoparticles were mixed with drill cuttings. The drill cuttings were from shale gas reservoir at different depths. An AS 5250 pyrolysis autosampler (commercially available from CDS Analystical LLC in Oxford, Pa.) interfaced to a portable high pressure G908 GCMS (commercially available from 908 Devices in Boston Mass.) was used to analyze the mixture. Pyrolyzed at 800° C. where interference from the decomposition of source rock is high, nanoparticles can be detected at <350 ppm. As shown in FIG. 4F, detectability of trimethylstyrene (TMS) was lower than the other styrenic monomers under these analysis conditions.

There are also several base monomer material options available with different ceiling temperatures, which allows for better discrimination of the pyrolyzed taggant material from the oil base of the mud and/or from kerogens and other hydrocarbons in the formation cuttings. This is particularly important if pyrolysis-GCMS is part of the rock evaluation workflow of the drill cuttings. Judicious choice of taggants with ceiling temperatures that do not interfere with pyrograms from source rock decomposition will enable correlation of location and composition of drill cuttings simultaneously.

Tests performed on drill cuttings from unconventional reservoirs injected with a small concentration of polymer taggants demonstrated the feasibility of identification of the taggants against background from pyrolysis of the drill cuttings without the need for pre-processing. Using polymeric taggants with different ceiling temperatures can reduce the likelihood that the polymeric taggants interfere with pyrograms from source rock decomposition.

Figure 5A:
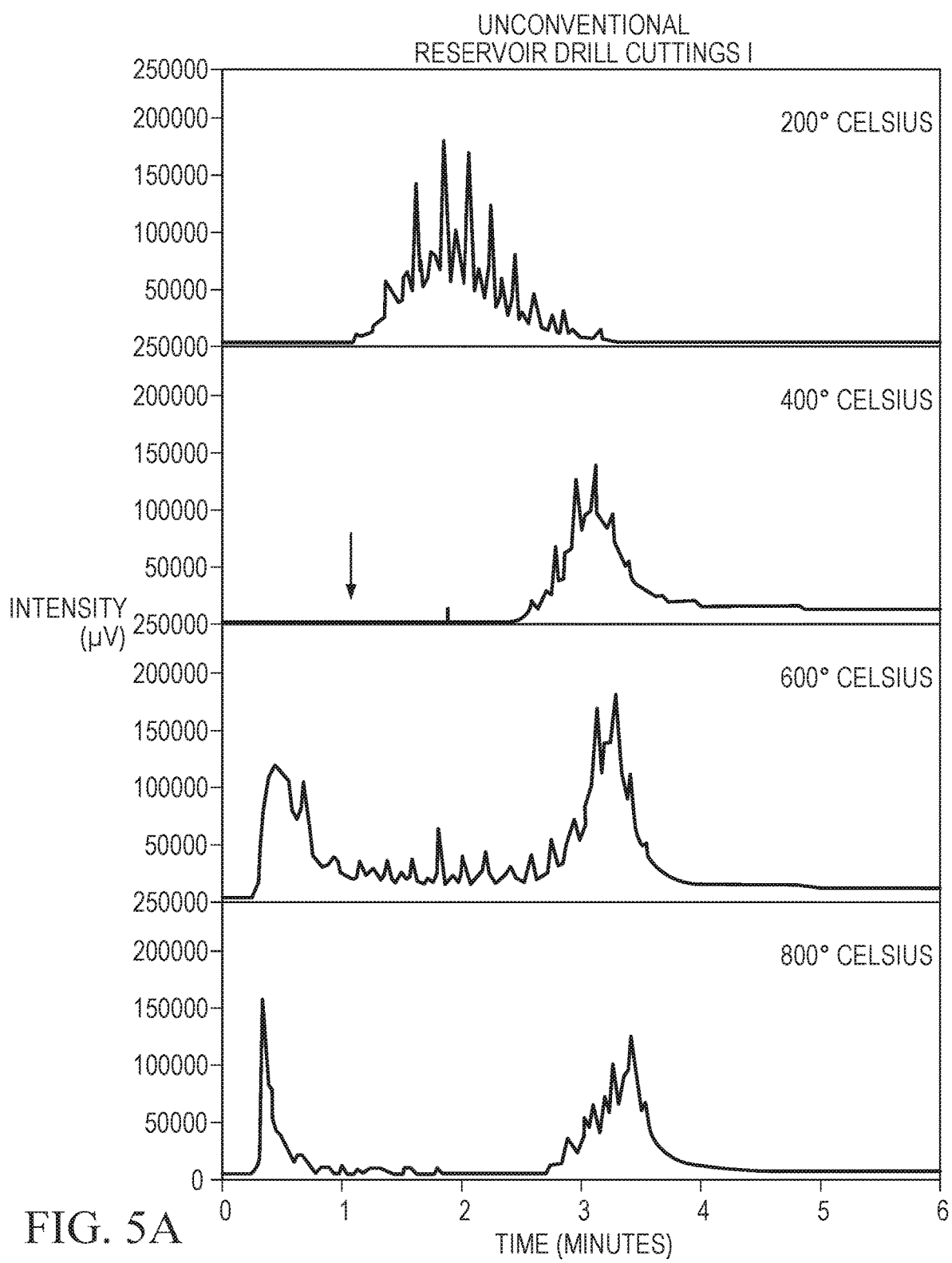
FIGS. 5A-5C show gas chromatograms of drill cuttings at different pyrolysis temperature stages.
Figure 5B:
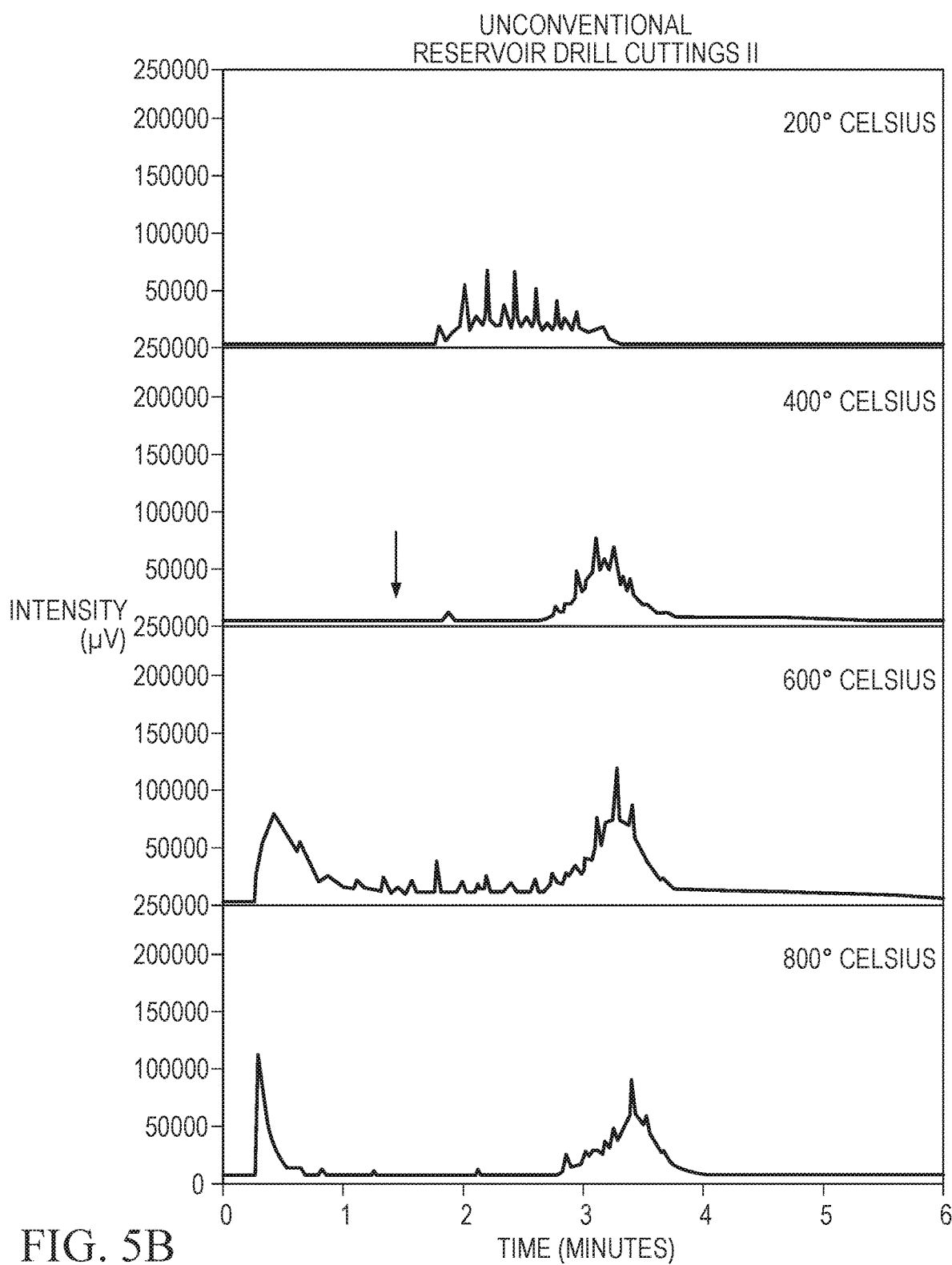
Figure 5C:
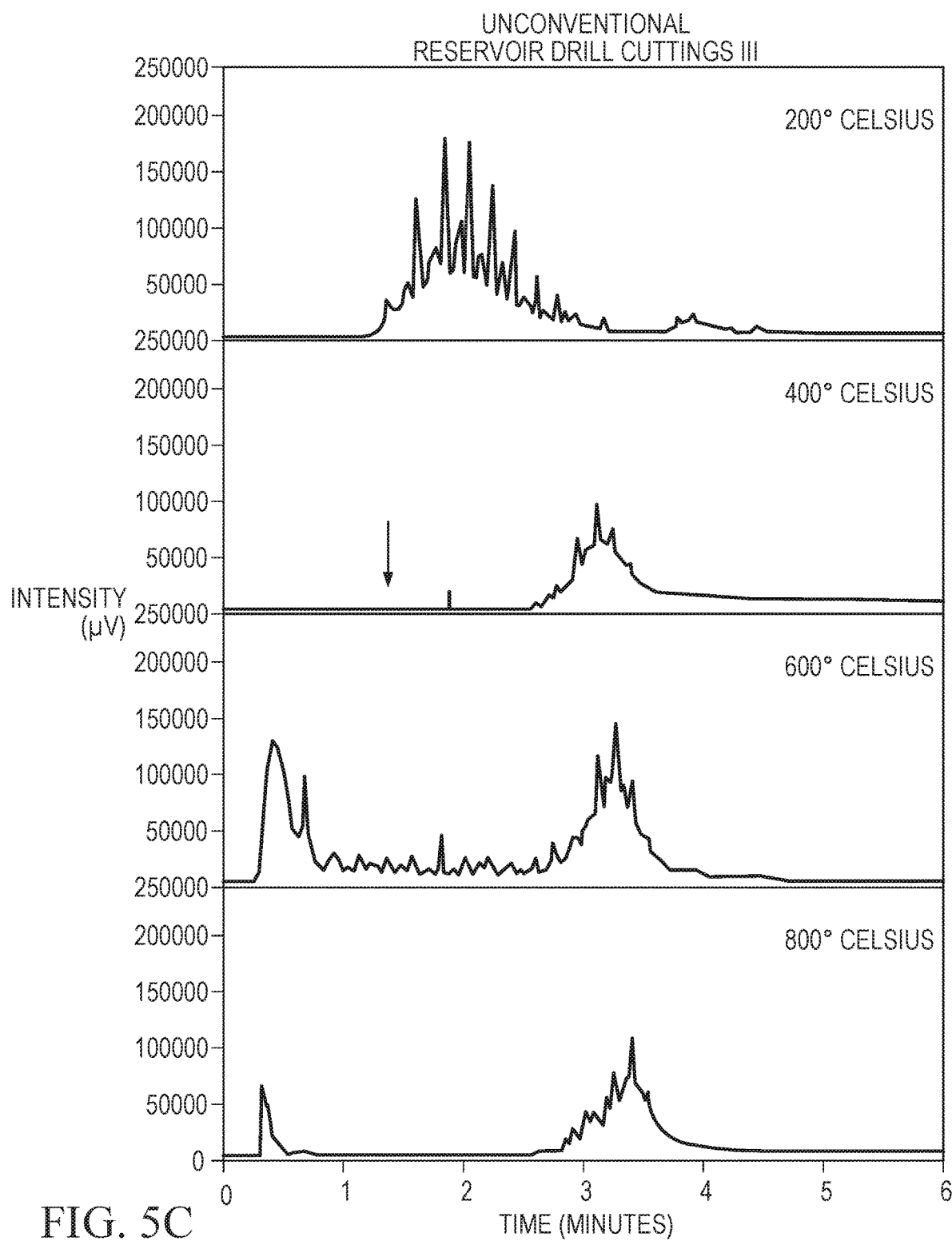

FIGS. 5A-5C show gas chromatograms of drill cuttings from an unconventional reservoir at different pyrolysis temperature stages. This test was performed on cuttings from different depths of an unconventional reservoir with conditions similar to those in Saudi Arabia. This test was performed using an AS 5250 pyrolysis autosampler (commercially available from CDS Analytical LLC in Oxford, Pa.) interfaced to a portable high pressure G908 GCMS (commercially available from 908 Devices in Boston Mass.). These chromatograms reveal a relatively low background window at the 1 to 2.5 minute elution time at 400° C. (indicated by arrows). At low temperatures (less than 200° C.), volatilization of light hydrocarbons, such as the diesel oil-based muds, occurs. At 600 to 800° C., decomposition of the source rock begins, liberating hydrocarbon. Volatilization occurs at all four temperatures. However, at the 400° C. range, there is a period between 1 and 2.5 minutes of elution time that is repeatable for all formation sample depths. In these tests, the volatiles coming off at 200° C. were from diesel used to clean the cuttings. The volatiles coming off at 400° C. after 2.5 minutes were from the decomposition of source rock. The low background windows indicate that selection of a depth taggant with a ceiling temperature between 200° C. and 400° C. and an elution time between 1 to 2.5 minutes would be appropriate for surface logging of these reservoirs using pyrolysis-gas chromatography-mass spectrometry analysis of drill cuttings.

Figure 6A:
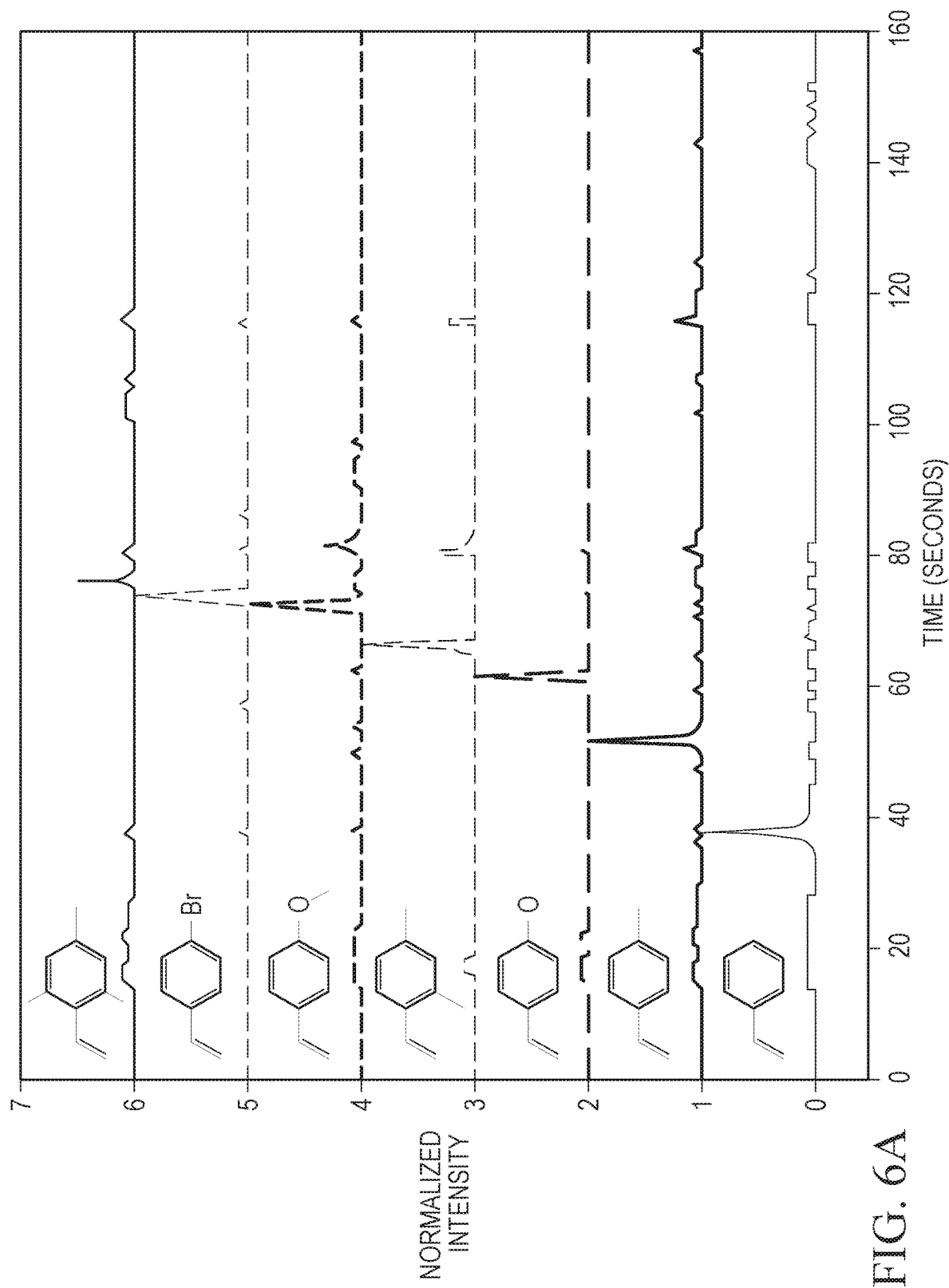
FIGS. 6A and 6B show pyrograms for styrenic and methacrylic nanoparticles.
Figure 6B:
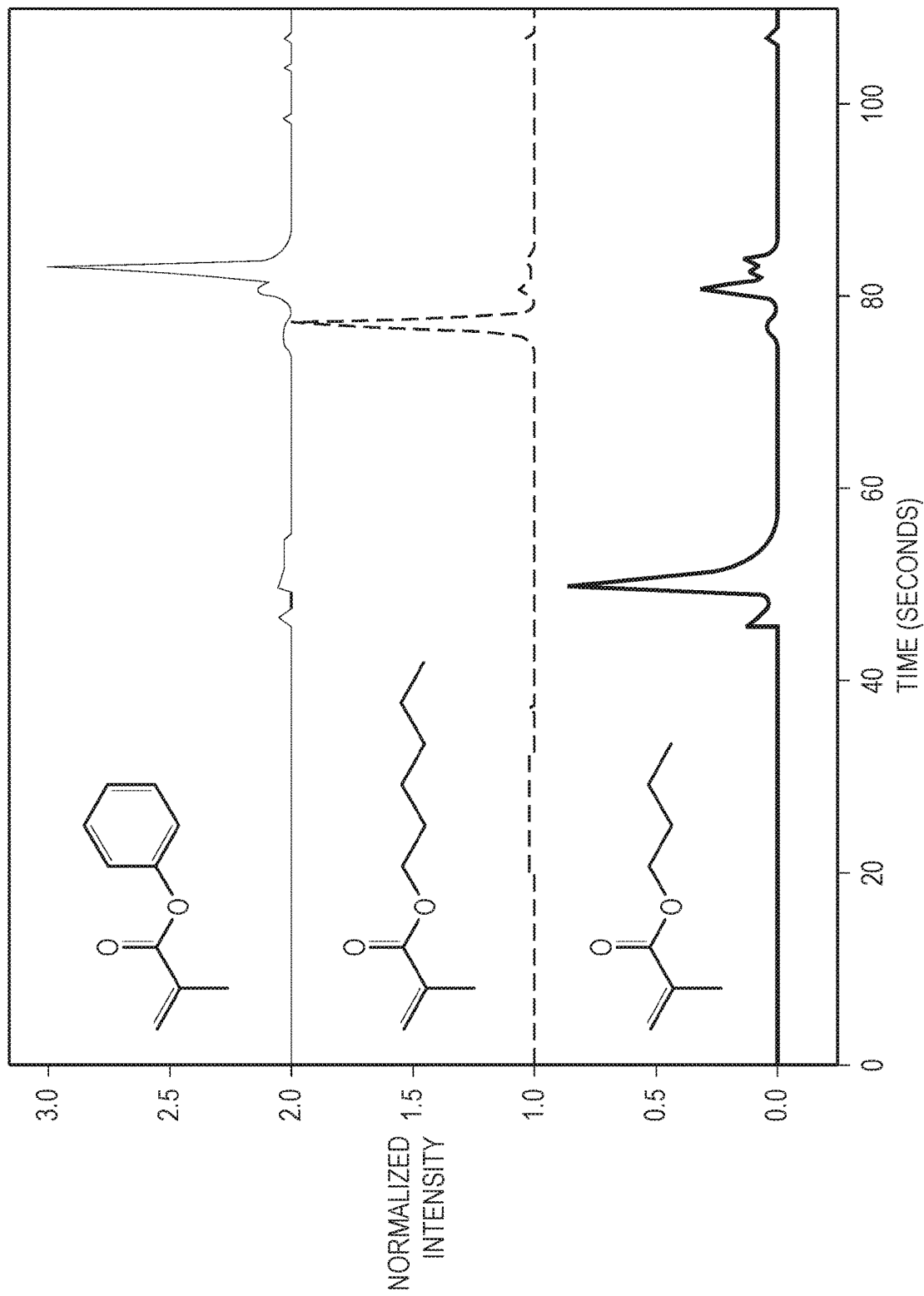

FIGS. 6A and 6B show pyrograms for styrenic and methacrylic nanoparticles. For the styrenic particles (FIG. 6A), drying was conducted at 400° C. for 20 seconds and pyrolysis was performed at 800° C. for 15 seconds. For the methacrylic nanoparticles (FIG. 6B), drying was conducted at 350° C. for 15 seconds and pyrolysis at 400° C. for 15 seconds. The styrenic polymers are examples of taggants with ceiling temperature between 600 and 800° C. and methacrylic monomer-based nanoparticle are examples of taggants that can be pyrolyzed at much lower temperatures. For cuttings from unconventional reservoir containing source rock, styrenic polymers with their higher ceiling temperature (Tc) at around 400° C. is not suitable as a taggant. However, styrenic polymers could be used for other reservoirs such as, for example, conventional sandstone or carbonate reservoirs. Methacrylate polymers with Tc around 200° C. may be more suitable as taggants for mud logging of shale reservoirs. As discussed with respect to FIGS. 5A-5C, the taggant for surface logging a reservoir can be chosen to provide a taggant that elutes in a low background time/temperature window for that particular reservoir. These results demonstrate the adaptability of the methods and systems previously described for performing surface logging on reservoirs whose rocks liberate hydrocarbons at different heating stages.

In contrast to elemental or ion taggants, the proposed amorphous polymeric material will not interfere with x-ray diffraction or other nuclear-based porosity or mineralogy analyses conventionally performed on reservoir rock cores and drill cuttings.

The characteristics of this approach can be useful when "missing-cutter" drill bits are used as the drill bit 118 when surface logging is being conducted to provide improved cuttings quality and size assurance. The polycrystalline diamond compact (PDC) bits routinely used to drill deeply buried hard rock formations generally shear the rock and create very small depth of cuts that render the cuttings extremely small (0.020 to 0.2 millimeters (mm)) and generally useless for mud logging applications such as, for example, formation mineralogy, porosity, and total organic carbon (TOC) determinations. Missing-cutter drill bits (which generally recess a few cutters at the center of the bits) were developed to allow larger cuttings (for example, 10 to 40 mm) that are well suited for surface logging applications to evolve. However, these missing-cutter drill bits only generate cuttings from only a limited fraction of the rock that is drilled through. Taggants that can be detected in small amounts facilitate depth correlation of the limited amount of larger cuttings generated when using missing-cutter drill bits.

A number of embodiments of the methods and systems have been described. Nevertheless, it will be understood that various modifications may be made without departing from the spirit and scope of this disclosure. Accordingly, other embodiments are within the scope of the following claims.

What is claimed is:

1. A method of surface logging a well using a plurality of polymeric taggants distinguishable from each other, the method comprising:
adding each of the plurality of polymeric taggants to a circulating drilling fluid in a sequence while drilling the well, wherein at least one of the plurality of polymeric taggants is in the form of a polymeric nanoparticle or a solubilized polymer; and wherein the polymeric taggants are added in pulses with a volume of one polymeric taggant of the plurality of polymeric taggants added to the drilling fluid followed by a pause before a volume of the next polymeric taggant in the sequence of the plurality of polymeric taggants is added to the drilling fluid
taking a sample of drill cuttings carried by the circulating drilling fluid;
measuring concentrations of individual polymeric taggants attached to the drill cuttings in the sample; and
identifying a depth associated with the sample based, at least in part, on the measured concentrations of individual polymeric taggants and on the sequence.

2. The method of claim 1, wherein the sequence is a repeating sequence including at least 5 polymeric taggants distinguishable from each other.

3. The method of claim 1, wherein portions of the polymeric taggants attach to the drill cuttings during generation of the drill cuttings.

4. The method of claim 3, wherein adding each of the plurality of polymeric taggants to the circulating drilling fluid comprises adding the polymeric nanoparticles to the circulating drilling fluid.

5. The method of claim 4, wherein the nanoparticles of the polymeric taggants penetrate into the drill cuttings.

6. The method of claim 1, wherein the polymeric taggants have ceiling temperatures between 400 and 800° C.

7. The method of claim 6, wherein the polymeric taggants comprise styrenic polymers with ceiling temperature between 600 and 800° C.

8. The method of claim 6, wherein the polymeric taggants comprise methacrylic polymers with ceiling temperature between 400 and 600° C.

9. The method of claim 1, wherein pyrolysis-gas chromatography-mass spectrometry is used to simultaneously measure concentrations of individual polymeric taggants attached to the drill cuttings and analyze properties of the drill cuttings.

10. The method of claim 1, further comprising performing nuclear-based porosity or mineralogy analyses on the drill cuttings.

11. The method of claim 1, wherein the polymeric taggants have an affinity for the drill cuttings.

12. The method of claim 11, wherein the polymeric taggants have a hydrophobic surface.

13. The method of claim 1, wherein taking the sample of the circulating drilling fluid comprises taking the sample before the drilling fluid returns to a mud pit or other reservoir.

14. The method of claim 1, wherein adding each of the plurality of polymeric taggants to a circulating drilling fluid comprises injecting fluid bearing the polymeric taggants at a concentration of between 500 and 1500 ppm at a rate of between 1 and 10 liters per minute into the mud-flow.

15. The method of claim 14, wherein injecting fluid bearing the polymeric taggants comprises injecting fluid bearing a first polymeric taggant for between 30 and 180 seconds before switching to a next polymeric taggant.

16. The method of claim 15, wherein switching to the polymeric taggant next in the sequence comprises waiting between 60 and 240 seconds after stopping injection of the first polymeric taggant before starting injection of the next polymeric taggant.

17. The method of claim 16, further comprising bagging cuttings at intervals of between 5 and 8 meters.

18. The method of claim 1, wherein the circulating drilling fluid comprises drilling mud.

19. The method of claim 1, wherein the circulating drilling fluid comprises foam.

20. A method of surface logging a well using a plurality of polymeric taggants distinguishable from each other, the method comprising:
adding each of the plurality of polymeric taggants to a circulating drilling fluid while drilling the well in a repeating sequence, wherein at least one of the plurality of polymeric taggants is in the form of a polymeric nanoparticle or a solubized polymer; and wherein the polymeric taggants are added in pulses with a volume of one polymeric taggant of the plurality of polymeric taggants added to the drilling fluid followed by a pause before a volume of the next polymeric taggant in the sequence of the plurality of polymeric taggants is added to the drilling fluid and
taking a sample drill cuttings carried by the circulating drilling fluid, wherein the plurality of polymeric taggants penetrate or adhere to the sample of drill cuttings;
wherein the polymeric taggants have ceiling temperatures between 400 and 800° C.

21. The method of claim 20, wherein adding each of the plurality of polymeric taggants to the circulating drilling fluid comprises the polymeric nanoparticles to the circulating drilling fluid.

22. The method of claim 21, wherein the polymeric taggants comprise styrenic polymers with ceiling temperature between 600 and 800° C.

23. The method of claim 21, wherein the polymeric taggants comprise methacrylic polymers with ceiling temperature between 400 and 600° C.

24. The method of claim 20, wherein the polymeric taggants have an affinity for the drill cuttings.

25. The method of claim 24, wherein the polymeric taggants have hydrophobic surface.

* * * * *